United States Patent [19]

Donawick et al.

[11] Patent Number: 5,163,923
[45] Date of Patent: Nov. 17, 1992

[54] APPARATUS FOR THE ADMINISTRATION OF FLUIDS TO A SMALL ANIMAL

[75] Inventors: William J. Donawick, West Chester, Pa.; Daniel E. Wallig, Newark, Del.

[73] Assignee: International Win, Ltd., Kennett Square, Pa.

[21] Appl. No.: 766,567

[22] Filed: Sep. 27, 1991

[51] Int. Cl.⁵ .............................................. A61M 5/00
[52] U.S. Cl. ...................................... 604/257; 119/72
[58] Field of Search .................. 604/257, 80, 81, 258, 604/262, 30; 119/72

[56] References Cited

U.S. PATENT DOCUMENTS

| | | |
|---|---|---|
| 3,201,148 | 5/1963 | Shurtleff . |
| 3,616,866 | 4/1971 | Verbeul . |
| 3,640,551 | 2/1972 | Shakesby . |
| 3,785,683 | 1/1974 | Adelhed . |
| 3,977,708 | 8/1976 | Jopp . |
| 4,014,568 | 3/1977 | Carter et al. . |
| 4,254,773 | 3/1981 | Waldbillig . |
| 4,296,949 | 10/1981 | Muetterles et al. . |
| 4,480,639 | 11/1984 | Peterson et al. . |
| 4,569,348 | 2/1986 | Hasslinger . |
| 4,610,245 | 9/1986 | Biearman . |
| 4,662,873 | 5/1987 | Lash et al. . |
| 4,699,613 | 10/1987 | Donawick et al. ............. 604/257 X |
| 4,955,643 | 9/1990 | Bona et al. . |
| 4,955,864 | 9/1990 | Hajduch . |
| 4,955,867 | 9/1990 | Endo . |

Primary Examiner—John D. Yasko
Attorney, Agent, or Firm—Ratner & Prestia

[57] ABSTRACT

Apparatus for the administration of fluids to an animal which permits movement of the animal within an enclosure without the development of kinks and twists in fluid flow tubing in the apparatus which would otherwise cut off fluid flow to the animal. A resiliently flexible coiled tube is mounted on a swivel unit to which fluid is supplied and through which fluid passes. The coiled tube uncoils and recoils as the animal moves. In addition, rotational movements by the animal are accommodated by the swivel unit.

9 Claims, 4 Drawing Sheets

APPARATUS FOR THE ADMINISTRATION OF FLUIDS TO A SMALL ANIMAL

BACKGROUND OF THE INVENTION

1. Field of the Invention

This invention relates to an apparatus for the administration of fluids to small animals placed in cages.

2. Description of the Prior Art

It is very often necessary to administer fluids such as blood, plasma, drugs, and food intravenously to small animals. Small animals, as used herein, is intended to include pets or companion animals, such as dogs and cats, other small animals, such as rabbits and guinea pigs, and animals raised for fur, such as minks and foxes, as well as very young humans, such as infants and premature babies. Essentially, the invention can be used with any animal confined to a small cage or enclosure where overhead space is insufficient to use other arrangements, such as the apparatus for the gravitational administration of fluids and drugs to large animals described in U.S. Pat. No. 4,699,613 to Donawick, et al. Whereas the invention described in U.S. Pat. No. 4,699,613 can be used where there is sufficient overhead room to hang IV bags, in the case of small animal treatment, there is generally not sufficient overhead room within the cage to hang free, rotating IV bags.

The need for rotation of the IV bag, or at least IV tubing, comes about because many animals tend to be active and will tangle the tubing, either on itself or around the animal. Thus, it is desirable to maintain the IV tubing out of the reach of the animal and to allow the tubing to rotate freely. In the above referenced patent, the IV tubing can rotate freely because the IV bags can rotate freely. However, because it is impractical to provide sufficient room to hang IV bags in small cages or enclosures, some other arrangement for allowing free movement and rotation of the IV tubing must be provided.

SUMMARY OF THE INVENTION

In accordance with the present invention, apparatus for the administration of fluids to an animal includes means for supplying a fluid and a swivel unit including (a) a base having a chamber in fluid communication with the fluid supply means, (b) a tubular member mounted in the base for free rotation with respect to the base and in fluid communication with the chamber, and (c) means for securing the base to an enclosure within which an animal can be placed. Also included in this apparatus are means for conducting fluid from the chamber in the base of the swivel unit to an animal placed in the enclosure. Such means include a resiliently flexible coiled tube in fluid communication with the tubular member in the swivel unit and a fluid delivery needle in fluid communication with the resiliently flexible coiled tube. This apparatus further includes means for securing the fluid conducting means to the animal.

DETAILED DESCRIPTION OF THE INVENTION

Figure 1:
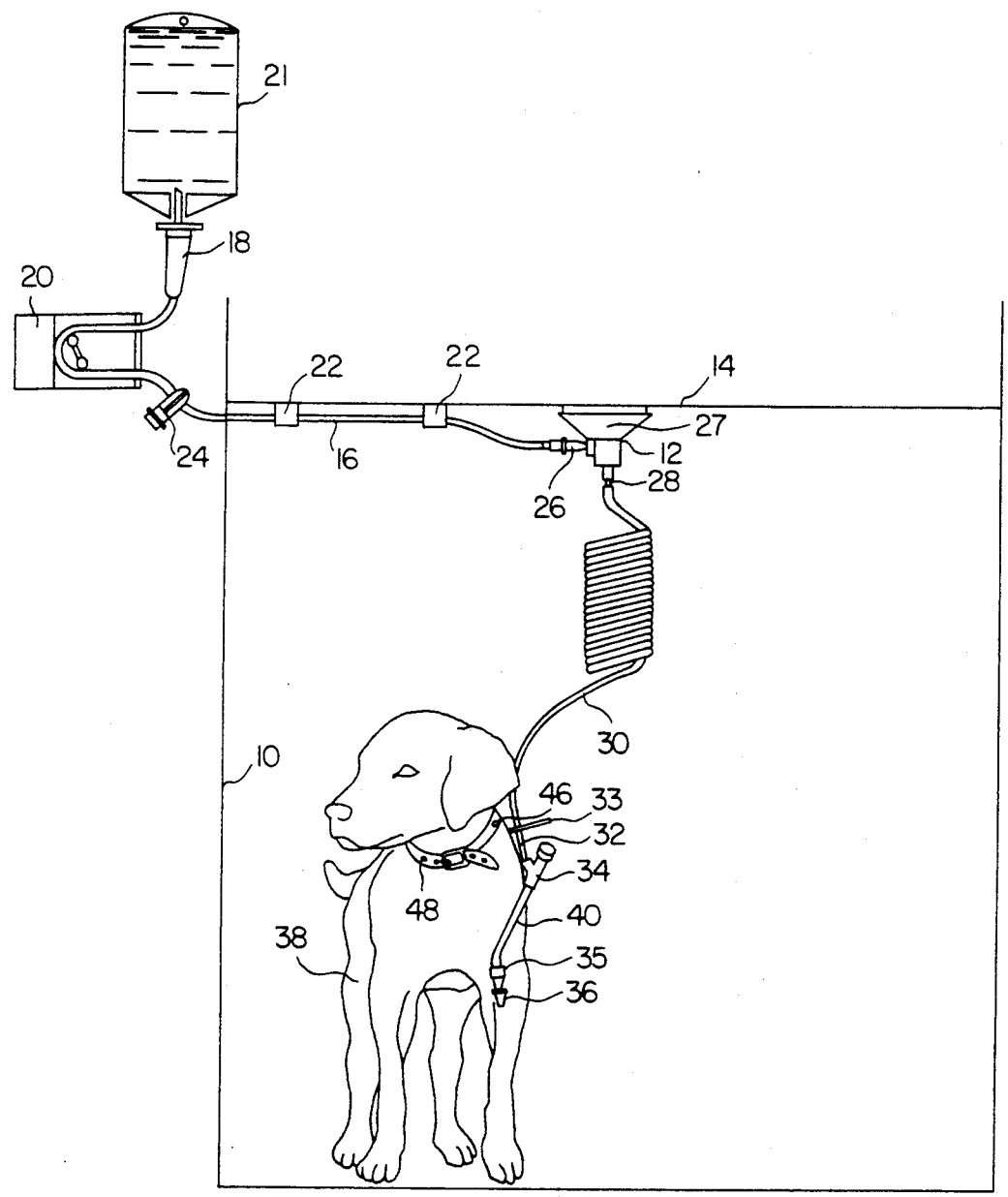
Figure 1 is a side view of fluid administration apparatus constructed in accordance with the present invention installed in a cage and connected to a small animal.

FIG. 1 shows apparatus, constructed in accordance with the present invention, mounted within an animal cage 10. This is accomplished by affixing a swivel unit 12 to the ceiling 14 of animal cage 10. Fluid is fed into swivel unit 12 through an IV tubing 16 which may be made of any standard material such as PVC. This tubing extends between a bag spike with drip chamber 18 to a fluid source and a luer connector 26 to swivel unit 12. IV tubing 16 can be supported by one or more tubing holders 22. The fluid source can be an infusion pump 20, an IV bag 21, or some other similar unit. In the case of IV bag 21, a flow restrictor 24 preferably is provided to reduce the fluid flow which would otherwise take place due to gravity feed. The fluid source, bag spike with drip chamber 18, IV tubing 16, flow restrictor 24 and luer connector 26 form a means for supplying a fluid to swivel unit 12.

Figure 2:
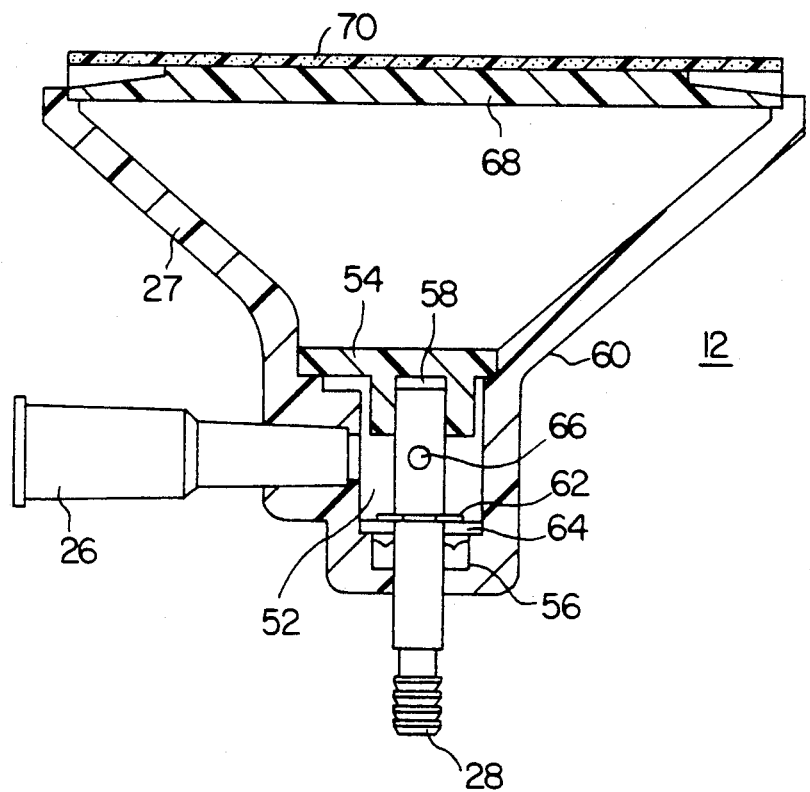
FIG. 2 is a cross sectional view of the swivel unit of the present invention.

As shown most clearly by FIG. 2, swivel unit 12 includes a base 27 having a chamber 52 which is in fluid communication with the fluid supply means, namely IV tubing 16 through luer connector 26. Swivel unit 12 also includes a tubular member, in the form of a hollow pin 28, mounted in base 27 for free rotation with respect to base 27. Hollow pin 28 is in fluid communication with chamber 52. Thus, fluid enters swivel unit 12 through luer connector 26 and exits swivel unit 12 through hollow pin 28.

Swivel unit 12 further includes means for securing base 27 to animal cage 10. Two arrangements for mounting swivel unit 12 to ceiling 14 of animal cage 10 will be described below.

Figure 3:
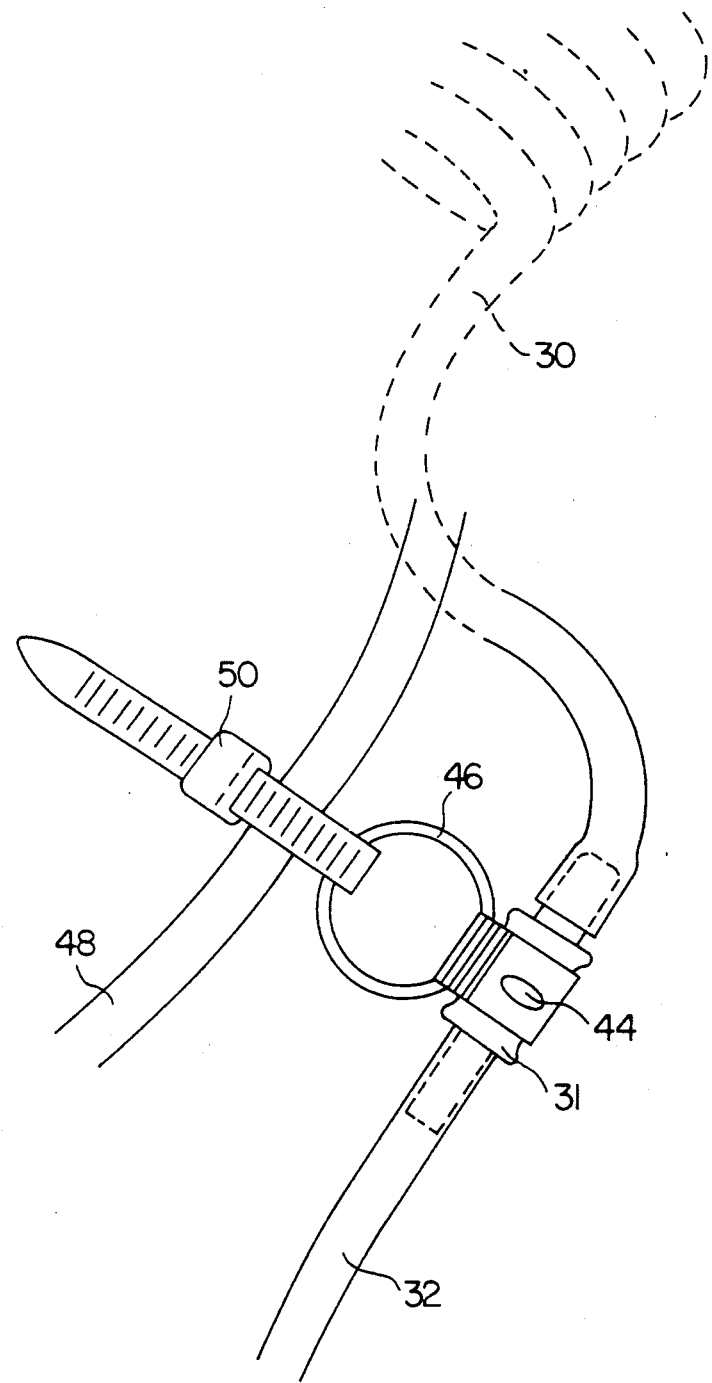
FIG. 3 is a plan view, on an enlarged scale, of that portion of the present invention by which the apparatus can be secured to an animal.

Fluid, exiting from chamber 52 through hollow pin 28, is conducted to an animal placed in cage 10. As shown by FIGS. 1 and 3, for the embodiment of the invention being described, fluid passes through a resiliently flexible coiled tube 30 which is connected to hollow pin 28, through a luer slip connector 31, through a length of IV tubing 32 and past a clamp 33, through an injection site 34, through a length of IV tubing 40, through a luer slip connector 35 and through an IV needle 36 into the patient 38, in this case a young dog. IV tubing 32 and IV tubing 40 may be made from any standard IV tubing material, such as PVC. However, it is quite important that coiled tube 30 be made from polyurethane or another material which is sufficiently flexible, holds its shape and resists kinking, so that as the animal moves farther from swivel unit 12, the coiled tube can uncoil and recoil as it moves with the animal. Also, as the animal walks in circles, coiled tube 30 transmits rotational torque to hollow pin 28 which is mounted for free rotation within base 27 of the swivel unit and which, in turn, is secured to ceiling 14 of the cage. When the force built up is great enough, hollow pin 28 swivels to release built up torque. This prevents kinking of coiled tube 30 and allows for a continuous fluid flow from the fluid source to the animal.

However, this requires that the means by which the fluid is conducted from swivel unit 12 to the animal be securely attached to the animal such that when the animal rotates in place, this rotation is transmitted directly to coiled tube 30 and does not affect the functioning of any of the components downstream from the coiled tube. One unit which can serve this purpose is shown in FIG. 3. As shown in FIG. 3, coiled tube 30 is attached to luer slip connector 31. When this connection is secure, coiled tube 30 will not rotate with respect to luer slip connector 31. Luer slip connector 31 is then secured by a crimp ring 44 to a split ring 46. Crimp ring 44 is securely attached to luer slip connector 31, and will also transmit rotational force to luer slip connector 31. Split ring 46 is, in turn, connected to a collar 48 worn by the animal patient (not shown in FIG. 3) by a releasable cable tie 50. This attachment allows transmission of force from the animal to coiled tube 30. IV tubing 32 is isolated from rotational torque because it is below luer slip connector 31 and is attached at its other end (with y-injection site 34 interposed) through luer slip connector 35 to IV needle 36 which is in the limb of animal patient 38. Split ring 46 is generally a detachable ring such as those commonly used for key chains.

As shown in FIG. 3, the entire length of coiled tube 30 is coiled, and the coil feeds directly into luer slip connector 31. Alternatively, the coiled tube may have a relatively straight end where it feeds directly into luer slip connector 31. It is very important, however, that the luer slip connector 31 be securely fastened to the collar of the animal in order to prevent any rotational force from being transmitted to IV tubing 32, because the IV tubing has a tendency to kink very easily, resulting in restriction or cessation of fluid flow to the animal.

Referring to FIG. 2, fluid enters swivel unit 12 through luer connector 26 and exits the swivel unit through rotatable hollow pin 28. Between these two components and in base 27 of the swivel unit is fluid chamber 52, which under operating conditions, will be full of fluid. The fluid is held in chamber 52 by an inner plug 54 and a seal 56. Rotatable hollow pin 28 is centered in a recess 58 in inner plug 54. Preferably, inner plug 54 is made of a polycarbonate such as LEXAN (trademark), available from General Electric Co., Polymers Product Dept., Pittsfield, Mass. 01201, which along with rotatable hollow pin 28, preferably made of a stainless steel, provides a very low coefficient of friction. Similarly, the body 60 of base 27 of swivel unit 12 also can be made from LEXAN. Rotatable hollow pin 28 is held in place at one end by inner plug 54, and at the other end by a retaining ring 62 in conjunction with a washer 64. Both washer 64 and retaining ring 62 are preferably made from stainless steel in order to be inert to whatever fluid is being administered to animal patient 38. Seal 56 is preferably a glycerin impregnated rubber seal, such as that available from Minnesota Rubber, Inc.. This helps decrease the friction between seal 56 and rotating pin 28. It should be understood that the rotation of hollow pin 28 should take place with as little torque as possible in order to decrease the chance of kinking of coiled tube 30.

Fluid entering from luer connector 26 into fluid chamber 52 passes to hollow rotatable pin 28 through a fluid inlet 66 which passes through the wall of hollow pin 28. Thus, in any rotational position, fluid may flow freely into and through hollow rotatable pin 28.

Swivel unit 12 may be mounted to the cage ceiling 14 by any conventional mounting means. FIG. 2 shows a mounting plate 68 and double sided foam tape 70, as that available from 3M Corporation, which allows mounting on a smooth cage ceiling. The space between mounting plate 68 and inner plug 54 permits various other mounting units which protrude into this space to be used. The space is sealed against fluid by inner plug 54. Finally, and very importantly, swivel unit 12 should be affixed to the cage ceiling 14 so firmly that rotation of the swivel unit with respect to the cage ceiling is impossible.

Figure 5:
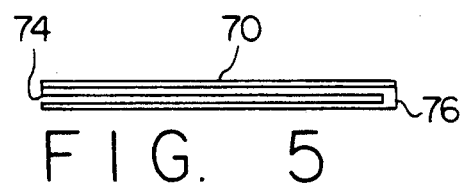
FIGS. 5 and 6 are side and bottom views, respectively, of a second arrangement of that portion of the present invention by which the apparatus can be secured to an enclosure within which an animal can be placed.
Figure 4:
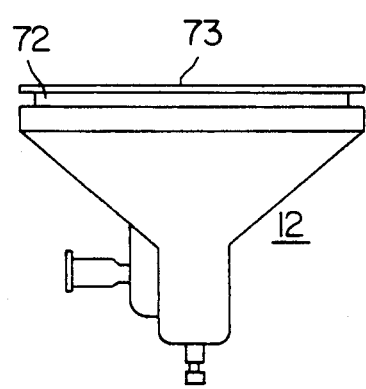
FIG. 4 is a side view of an alternative arrangement of the swivel unit of the present invention.
Figure 6:
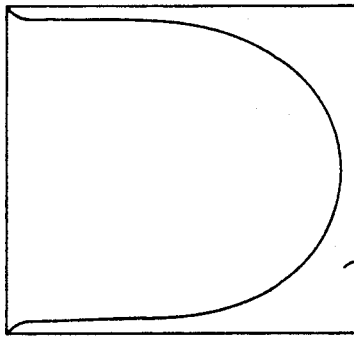

An alternative mounting arrangement is shown in FIGS. 4, 5, and 6. In this case, swivel unit 12 has a peripheral groove 72 between a flanged upper piece 73 the body of the swivel unit. The flanged upper piece fits into a slot 74 in a mounting bracket 76 which is secured firmly to cage ceiling 14 with double sided foam tape such as that available from 3M Corporation. In this way, swivel unit 12 may be removed and replaced easily.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed:

1. Apparatus for the administration of fluids to an animal in an enclosure, comprising:
   means for supplying a fluid;
   a swivel unit including:
      (a) a base having a chamber in fluid communication with said fluid supply means,
      (b) a tubular member mounted in said base for free rotation with respect to said base and in fluid communication with said chamber, and
      (c) means for securing said base to an enclosure within which an animal can be placed;
   means, including:
      (a) a resiliently flexible coiled tube in fluid communication with said tubular member of said swivel unit, and
      (b) a fluid delivery needle in fluid communication with said resiliently flexible coiled tube, for conducting fluid from said chamber in said base of said swivel unit to an animal placed in said enclosure; and
   means for securing said fluid conducting means to said animal.

2. The apparatus of claim 1 wherein:
   said fluid conducting means further includes, between said coiled tube and said fluid delivery needle, a second flexible tube, rigidly and fluidly connected to said coiled tube, and
   said means for securing said fluid conducting means to an animal is connected to said fluid conducting means at said rigid fluid connection between said flexible tubes.

3. The apparatus of claim 2 wherein said securing means comprises an annularly recessed groove in said base, and a mounting bracket adapted to receive said groove.

4. Apparatus for the administration of fluids to an animal in an enclosure, comprising:
- a fluid source including a fluid source tube projecting therefrom;
- a swivel unit secured to an overhead portion of said enclosure, said swivel unit including:
  a) a fluid chamber fluidly connected to said fluid source tube; and
  b) a freely rotating hollow pin projecting downwardly from said swivel unit, having one end fluidly connected to said fluid chamber and having a fluid path therethrough;
- a first resilient coiled delivery tube fluidly connected to said hollow pin;
- a second resilient flexible tube rigidly and fluidly connected to said first resilient coiled delivery tube;
- a fluid delivery needle fluidly connected to said second resilient flexible tube; and
- an attachment between said rigid connection and said animal.

5. The apparatus of claim 4 wherein said fluid source is an infusion pump.

6. The apparatus of claim 4 wherein said fluid source is an IV bag.

7. The apparatus of claim 4 wherein said attachment is a split ring and cable tie and is attached to said animal at a collar.

8. The apparatus of claim 4 wherein said swivel unit is permanently secured to said enclosure.

9. The apparatus of claim 4 wherein said swivel unit includes an annular groove and said swivel unit is secured to said enclosure with a mounting bracket adapted to slidably receive said said swivel unit and annular groove.

* * * * *